United States Patent [19]

Immel et al.

[11] Patent Number: 5,245,082

[45] Date of Patent: Sep. 14, 1993

[54] PROCESS FOR THE PRODUCTION OF DI-(4-AMINOCYCLOHEXYL)-METHANE CONTAINING 15 TO 25% BY WEIGHT OF THE TRANS-TRANS ISOMER

[75] Inventors: Otto Immel; Gerhard Darsow, both of Krefeld; Rudolf Braden, Odenthal; Hans-Helmut Schwarz, Krefeld; Helmut Waldmann, Leverkusen, all of Fed. Rep. of Germany

[73] Assignee: Bayer Aktiengesellschaft, Leverkusen, Fed. Rep. of Germany

[21] Appl. No.: 4,382

[22] Filed: Jan. 14, 1993

Related U.S. Application Data

[63] Continuation of Ser. No. 752,145, Aug. 29, 1991, abandoned.

[30] Foreign Application Priority Data

Sep. 6, 1990 [DE] Fed. Rep. of Germany ....... 4028270

[51] Int. Cl.$^5$ ............................................. C07C 209/72
[52] U.S. Cl. ..................................... 564/451; 564/450; 564/452
[58] Field of Search ........................ 564/450, 451, 452

[56] References Cited

U.S. PATENT DOCUMENTS

| | | | |
|---|---|---|---|
| 2,166,971 | 7/1939 | Schmidt et al. | 564/450 |
| 3,153,088 | 10/1964 | Arthur | 564/452 |
| 3,155,724 | 11/1964 | Arthur | 564/444 |
| 3,636,108 | 1/1972 | Brake | 564/450 |
| 3,644,272 | 2/1972 | Otis | 524/482 |
| 3,644,522 | 2/1972 | Brake et al. | 564/450 |
| 3,697,449 | 10/1972 | Brake | 564/451 |
| 3,766,272 | 10/1973 | Brake | 564/444 |
| 4,394,523 | 7/1983 | Allen | 564/451 |
| 4,429,155 | 1/1984 | Göetz et al. | 564/402 |
| 4,943,549 | 7/1990 | Immel et al. | 502/304 |

FOREIGN PATENT DOCUMENTS

324190 7/1989 European Pat. Off. .
1150380 4/1969 United Kingdom .

Primary Examiner—Glennon H. Hollrah
Assistant Examiner—Scott C. Rand
Attorney, Agent, or Firm—Joseph C. Gil; N. Denise Brown

[57] ABSTRACT

Di-(4-aminocyclohexyl)-methane containing 15 to 25% by weight of the trans-trans isomer can be obtained by the catalytic hydrogenation of di-(4-aminophenyl)-methane at elevated temperature and elevated hydrogen pressure in the presence of a ruthenium-containing supported catalyst containing 0.05 to 5% by weight ruthenium on an Al$_2$O$_3$ support which has been treated with compounds of rare earth metals and manganese.

13 Claims, No Drawings

PROCESS FOR THE PRODUCTION OF DI-(4-AMINOCYCLOHEXYL)-METHANE CONTAINING 15 TO 25% BY WEIGHT OF THE TRANS-TRANS ISOMER

This application is a continuation of application Ser. No. 07/752,145 filed Aug. 29, 1991 now abandoned.

BACKGROUND OF THE INVENTION

The present invention relates to an improved process for the production of a liquid mixture of the isomers of di-(4-aminocyclohexyl)-methane by hydrogenation of di-(4-aminophenyl)-methane ("MDA"). The liquid isomer mixture obtainable in accordance with the invention contains from 15 to 25% by weight and preferably from 18 to 23.5% by weight of the trans-trans isomer.

A liquid isomer mixture of the type noted above is generally required for the production of an isocyanate derivative which in turn is liquid at room temperature (approximately 10 to 25° C.).

In general, the hydrogenation of MDA leads to an isomer mixture in which the cis-cis isomer, the cis-trans isomer and the trans-trans isomer occur together and in which the trans-trans content approaches the equilibrium concentration of around 50% by weight. An isomer composition with the relatively low trans-trans isomer content mentioned above (i.e., from 15 to 25% by weight) can be produced by the complicated conversion process described in German Auslegungschrift 1,593,293. There are other known processes which allow for the preparation of an isomer mixture of di-(4-aminocyclohexyl)-methane containing a specific amount of the trans-trans isomer (see, e.g., U.S. Pat. Nos. 3,766,272, 3,644,522, 3,155,724, and 3,153,088). European Patent 324,190 describes a hydrogenation process for MDA which produces hydrogenation products wherein the trans-trans content corresponds to the desired value. The process requires the use of special catalysts and the maintenance of certain reaction conditions. However, this process has the disadvantage that the overall yield of di-(4-aminocyclohexyl)-methane is unsatisfactory. In addition, some of the hydrogenation or conversion processes mentioned must be carried out in the presence of ammonia or high-grade solvents.

Accordingly, the problem addressed by the present invention was to provide a new, simplified and industrially workable process in which the trans-trans isomer content would be in the desired range mentioned above with a high overall conversion. This problem has been solved by the process according to the invention.

DESCRIPTION OF THE INVENTION

The present invention is directed to a process for the production of di-(4-aminocyclohexyl)-methane containing from 15 to 25% by weight of the trans-trans isomer by the catalytic hydrogenation of di-(4-aminophenyl)-methane at elevated temperature and elevated hydrogen pressure in the presence of a ruthenium-containing supported catalyst. The process of the invention is characterized by the use of a ruthenium catalyst on an $Al_2O_3$ support which has been treated with compounds of rare earth metals and manganese. The ruthenium content of the catalyst used herein is from 0.05 to 5% by weight, preferably from 0.05 to 3% by weight and most preferably from 0.1 to 2% by weight, based on the total weight of the catalyst.

Accordingly, the process of the invention is characterized by the use of a special ruthenium supported catalyst wherein the support, $Al_2O_3$, contains compounds of rare earth metals and manganese. An addition of basic alkali compounds produces further improvements.

The $Al_2O_3$ is preferably α- or γ-$Al_2O_3$ and, most preferably, is γ-$Al_2O_3$.

The combined content of rare earth metal and manganese is from 0.05 to 8% by weight and preferably from 0.2 to 5% by weight, based on the total weight of the catalyst. The weight ratio of rare earth metal to manganese is from 5:1 to 1:5 and preferably from 2:1 to 1:2.

The rare earth metals are the elements of the IIIb group of the Periodic system. These include materials such as scandium, yttrium, lanthanum and the lanthanides. Either one or a mixture of two or more of the rare earth metals may be used. Crude mixtures of rare earth metals of the type which are commercially available and in which only one or two of the rare earth metals is/are initially enriched can also be used. It is preferred to use one or more of the elements selected from the group consisting of yttrium, lanthanum, cerium, praseodymium, neodymium and dysprosium. In a particularly preferred embodiment, cerium, lanthanum or a mixture thereof is used. In an especially preferred embodiment, cerium, which may be in the form of a cerium-enriched mixture, is used. The rare earth metals and manganese are present in the form of their compounds, preferably in oxide form, for treating the $Al_2O_3$ support.

The oxides, hydroxides or carbonates of the alkali metals, preferably NaOH and KOH, may be used as basic additives. The basic additives may be applied to the catalyst support before or after the treatment with the rare earth metals and manganese. The alkali metal addition is preferably between 0.1 and 10% and more preferably between 0.2 to 5%, based on the weight of the catalyst.

The catalyst useable in accordance with the invention may be prepared, for example, by applying compounds of the rare earth metals and manganese to an $Al_2O_3$ in the form of extrudates, pellets or spheres of between about 2 and 10 mm in size. The support thus treated is dried and then further treated with a ruthenium salt, followed by another drying step. In a preferred embodiment, the catalyst support initially treated with rare earth metals and manganese is heated to a temperature of 200° to 450° C. before the ruthenium is applied.

Compounds of the rare earth metals and manganese may be applied, for example, by impregnation or spraying with suitable salts of the elements mentioned. The salts of the rare earth metals and manganese are converted into compounds which adhere firmly to the catalyst support by a suitable drying temperature and, in a preferred embodiment, by heating to between 200° and 450° C. However, compounds of the rare earth metals and manganese may also be applied by co-precipitation of a rare earth metal/manganese hydroxide mixture from rare earth metal and manganese salts onto the impregnated support with alkali hydroxide or ammonia, optionally followed by removal of the soluble components by washing with water. Suitable salts of the rare earth metals and manganese are, in particular, the sulfates, chlorides, acetates and/or nitrates. The support treated with rare earth metals and manganese is first dried and then heated, preferably for 1 to 120 hours at 200° to 450° C. and preferably at 250° to 430° C. The temperature may be increased from lower to higher values within these ranges over the period of time mentioned.

The support thus treated may be subsequently impregnated with ruthenium by applying the ruthenium to the support, for example in the form of an aqueous solution of the chloride, nitrate, acetate or any other suitable salt, by impregnation or spraying, again followed by drying. Before drying, however, the ruthenium-impregnated support may also be treated with a solution of the basic compounds mentioned above, the ruthenium precipitating in the form of the oxide or hydroxide. The water-soluble components may then be removed by washing, followed by drying. Thereafter a catalyst suitable for use in accordance with the invention is available. In a preferred embodiment, however, the catalyst is activated before use, preferably after arrangement in the hydrogenation reactor, by treatment with hydrogen at a temperature in the range from 150° to 350° C. After activation, it may again be desirable to remove anions, such as chloride, nitrate, acetate or others, and optionally the cations of the basic compounds used for precipitation by washing with water. However, the catalyst support treated with compounds of the rare earth metals and manganese may also first be impregnated with a solution of one of the basic compounds mentioned, and subsequently dried. Solutions of ruthenium salts may then be applied to the basified catalyst support, the ruthenium being precipitated in the form of its oxide or hydroxide at the moment of impregnation. In this case, too, the catalyst is ready for use after drying, although it is preferably first activated with hydrogen in the manner described above. In this variant, too, the ruthenium supported catalyst is ready for use despite the presence of the residues of such alkaline compounds. In a preferred embodiment, however, it is washed with water as described above.

The application of the various substances to the $Al_2O_3$ support by impregnation or spraying and the apparatus required for this purpose are known in the art. It is also known that the required degree of application can be adjusted through the choice of the quantity and concentration of the solutions of the elements mentioned.

The hydrogenation reaction according to the invention takes place at a temperature in the range from 80° to 160° C. and preferably at a temperature in the range from 90° to 140° C. The choice of the temperature is determined by the required reaction rate and also by the desired composition of the isomer mixture. The reaction rate increases with increasing temperature, as does the trans-trans content of the isomer mixture formed. The catalyst has an isomerizing effect on the hydrogenation product, particularly at relatively high temperatures, so that the trans-trans content can increase even further in the event of prolonged contact. Accordingly, it is generally preferable to remove the hydrogenation product from the catalyst after the uptake of hydrogen has stopped.

According to the invention, the hydrogen pressure applied is in the range from 20 to 500 bar and preferably in the range from 200 to 400 bar. The higher the hydrogen pressure, the faster the hydrogenation reaction. By applying a relatively high hydrogen pressure, therefore, it is possible to keep to a relatively low hydrogenation temperature and/or a relatively short contact time with the catalyst in order to reduce the trans-trans content of the hydrogenation product.

Where hydrogenation is carried out discontinuously in an autoclave, the course of the reaction can be followed and, thus, the end of the hydrogenation time can be determined from the amount of hydrogen taken up. The hydrogenation time is generally between 2 and 5 hours, depending on the quantity of catalyst and the temperature applied.

In a particularly advantageous embodiment, the process is conducted continuously. The catalyst can be introduced in the form of granules into a vertical pressure tube. The MDA to be hydrogenated, optionally together with an inert solvent for dilution, and the hydrogen are passed through the catalyst bed from above. The hydrogen removed from the reaction product discharged may be reused for the reaction. Under given reaction conditions, the most favorable throughput rate can be established and followed by gas-chromatographic analysis ("GC" analysis) of the hydrogenation product. A catalyst load of 0.05 to 0.5 kg MDA per liter catalyst per hour has proven to be particularly advantageous.

Suitable inert diluents are liquid compounds, such as dioxane, tetrahydrofuran, isobutanol or tert-butanol, which are known to the art as being inert to hydrogenation. In a preferred embodiment, however, part of the hydrogenation product may be used for dilution, eliminating the need to introduce a diluent from outside the system. Where an inert diluent/solvent or the hydrogenation product formed is used for dilution, the weight ratio of MDA to diluent is generally from 1:0.2 to 1:2 and preferably from 1:0.5 to 1:1.

Compared with known processes, the process according to the invention has the advantage of a higher yield in conjunction with the direct establishment of the desired isomer ratio and the use of a ruthenium catalyst which is easy to produce.

In the following Examples, all percentages are by weight.

EXAMPLES

Example 1

200 g of a commercially available $\gamma$-$Al_2O_3$ having a specific surface of 350 m$^2$/g and a bead diameter of 2 to 6 mm were impregnated with a solution which had been prepared from 12.4 g $Ce(NO_3)_3.6H_2O$, 18.28 g $Mn(NO_3)_2.4H_2O$ and 50 g water. The impregnated $Al_2O_3$ was dried for 18 hours at 120° C. in a water jet vacuum and then heated for 3 hours at 400° C. The catalyst support thus produced was impregnated with 70 g of an aqueous $RuCl_3$ solution containing 2 g Ru. The moist catalyst was dried for 18 hours at 120° C. in a water jet vacuum and activated for 3 hours at 350° C. in a stream of hydrogen (100 liters $H_2$/hour).

Example 2

25 ml (19 g) of the Ru-Ce-Mn-$Al_2O_3$ catalyst prepared in accordance with Example 1 containing 1% Ru, 2% Ce and 2% Mn were used for the hydrogenation of di-(4-aminophenyl)-methane (MDA) in a 0.25 liter shaker autoclave. A sieve basket filled with the catalyst was arranged inside the autoclave. 40 g MDA dissolved in 40 g tert-butanol were hydrogenated six times in succession with this catalyst filling. The hydrogen pressure was 260 to 300 bar and the reaction temperature was 140° C. The necessary hydrogenation time was between 240 and 300 minutes. After each hydrogenation, the autoclave was cooled to room temperature; the reaction product was removed and the autoclave was refilled with a solution of MDA in tert-butanol. The reaction products were analyzed for their content of trans-trans isomer and di-(4-aminocyclohexyl)-methane ("HMDA"). The results obtained are shown in the following Table (the amount of trans-trans isomer is based on the amount of the HMDA):

| Hydrogenation time (mins.) | Trans-trans isomer (%) | 3- and 4-Nuclear compounds (%) | HMDA (%) |
|---|---|---|---|
| 300 | 22.5 | 2.8 | 96.5 |
| 265 | 19.8 | 2.6 | 96.9 |
| 240 | 19.0 | 1.7 | 97.9 |
| 270 | 21.0 | 1.5 | 98.3 |
| 260 | 20.6 | 1.9 | 97.7 |

Example 3

150 g of the catalyst prepared in accordance with Example 1 were aftertreated by impregnation with a solution which had been prepared from 54 g water and 6 g NaOH. The quantity of sodium hydroxide used corresponded to the absorption capacity of the catalyst. The impregnated catalyst was dried for 20 hours at 100° C. 60 ml (53 g) of the catalyst thus produced were arranged in a vertical pressure tube (diameter 14 mm, length 70 cm) which was heated by an oil thermostat. The spaces in the catalyst layer were filled with fine sea sand (0.2 to 0.3 mm).

A mixture of 1 part by weight MDA and 1 part by weight tert-butanol was introduced onto the catalyst from above together with hydrogen at 270 bar/112° C. The liquid trickled downwards through the catalyst into a separator. 30 to 50 liters hydrogen/hour were removed at the head of the separator. The MDA throughput corresponded to a catalyst load of 0.11 to 0.13 g MDA/ml cat. per hour and was kept in this range.

After 333 hours, the reaction product had the following composition according to analysis by gas chromatography:

| Trans-trans isomer: | 18.2% |
|---|---|
| 3- and 4-nuclear compounds: | 0.25% |
| Di-(4-aminocyclohexyl)-methane | 98.9% |
| Secondary products | 0.85% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the production of di-(4-aminocyclohexyl)-methane containing 15 to 25% by weight of the trans-trans isomer comprising catalytically hydrogenating di-(4-aminophenyl)-methane at a temperature in the range of 80° to 160° C. and hydrogen pressure in the range of from 20 to 500 bar in the presence of a catalyst, the improvement wherein said catalyst is a ruthenium catalyst on an $Al_2O_3$ support which has been treated with compounds of rare earth metals and manganese in a weight ratio of rare earth metal to manganese of from 5:1 to 1:5 and in a combined content of rare earth metal and manganese of from 0.05 to 8% by weight, the ruthenium content of said catalyst being from 0.05 to 5% by weight, based on the total weight of said catalyst.

2. The process of claim 1, wherein the ruthenium content is from 0.05 to 3% by weight.

3. The process of claim 2, wherein the ruthenium content is from 0.1 to 2% by weight.

4. The process of claim 1, wherein said combined content is from 0.2 to 5% by weight and said ratio is from 2:1 to 1:2.

5. The process of claim 1, wherein the treated catalyst support is heated to a temperature of from 200° to 450° C. and the ruthenium is subsequently applied.

6. The process of claim 5, wherein the treated catalyst support is heated to a temperature of from 250° to 430° C.

7. The process of claim 1, wherein the rare earth metal is one or more elements selected from the group consisting of yttrium, lanthanum, cerium, praseodymium, neodymium and dysprosium.

8. The process of claim 7, wherein the rare earth metal is cerium and/or lanthanum.

9. The process of claim 1, wherein the catalyst contains an oxide, hydroxide or carbonate of an alkali metal.

10. The process of claim 1, wherein the $Al_2O_3$ is used in $\alpha$- or $\gamma$-$Al_2O_3$.

11. The process of claim 1, wherein, before the hydrogenation of di-(4-aminophenyl)-methane, the catalyst is activated by treatment with hydrogen at 150° to 350° C.

12. The process of claim 1, wherein the reaction is carried out continuously, and a catalyst load of 0.05 to 0.5 kg di-(4-aminophenyl) methane per liter catalyst per hour is maintained.

13. The process of claim 1, wherein the di-(4-aminophenyl)-methane to be hydrogenated is used in admixture with a solvent/diluent in a weight ratio of from 1:0.2 to 1:2, and the solvent/diluent used is selected from the group consisting of dioxane, tetrahydrofuran, isobutanol, tert-butanol or the hydrogenation mixture formed.

* * * * *